US 6,632,177 B1

(12) United States Patent
Phillips et al.

(10) Patent No.: US 6,632,177 B1
(45) Date of Patent: Oct. 14, 2003

(54) DUAL PROCESS ULTRASOUND CONTRAST AGENT IMAGING

(75) Inventors: Patrick J. Phillips, Sunnyvale, CA (US); Ismayil M. Guracar, Redwood City, CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 10/136,935

(22) Filed: May 1, 2002

(51) Int. Cl.[7] .................................................. A61B 8/14

(52) U.S. Cl. ..................................................... 600/458

(58) Field of Search ................................ 600/458, 437, 600/442, 447, 440, 441, 443, 439; 73/625, 626, 602

(56) References Cited

U.S. PATENT DOCUMENTS

| | | |
|---|---|---|
| 5,577,505 A | 11/1996 | Brock-Fisher et al. |
| 5,632,277 A | 5/1997 | Chapman et al. |
| 5,706,819 A | 1/1998 | Hwang et al. |
| 5,951,478 A | 9/1999 | Hwang et al. |
| 5,961,460 A | 10/1999 | Guracar et al. |
| 6,095,980 A | 8/2000 | Burns et al. |
| 6,193,663 B1 | 2/2001 | Napolitano et al. |
| 6,213,947 B1 | 4/2001 | Phillips |
| 6,241,674 B1 | 6/2001 | Phillips et al. |
| 6,340,348 B1 * | 1/2002 | Krishnan et al. ............ 600/447 |
| 6,494,841 B1 * | 12/2002 | Thomas et al. .............. 600/447 |
| 6,497,666 B1 * | 12/2002 | Phillips et al. .............. 600/458 |

OTHER PUBLICATIONS

"Higher Order Nonlinear Ultrasonic Imaging," by Bruno Haider and Richard Y. Chiao (GE Corporate Research and Development, Niskayuna, NY 12309), 1999 IEEE ultrasonics Symposium (p. 1527–1531).

* cited by examiner

*Primary Examiner*—Marvin M. Lateef
*Assistant Examiner*—Ruby Jain

(57) ABSTRACT

Methods and systems for detecting contrast agents is provided. Differences between different sized vessels throughout a period of contrast agent enhancement are identified without significantly depleting the available contrast agent. Dual detection paths are used for imaging, such as one path for detecting nonlinear response and another path for detecting differences between the responses to two or more pulses. Where echoes from two or more pulses of acoustic energy are combined to detect the nonlinear response, the nonlinear response may also include signals originating from a loss-of-correlation (LOC) or motion between received pulses. These signals generated from LOC or motion can be produced from agent disruption where a second received echo is different from a first received echo due to a change in a bubble's shape (i.e., destruction), or from simple spatial translation between acoustic pulses as seen from the same spatial location, respectively. Together the LOC or motion signals and the nonlinear signals can differentiate contrast agent from tissue. Additional information is gained by detecting signals more responsive to difference or motion information. Each path detects different relative amounts of nonlinear response and responses caused by differences between echo signals of multiple pulses. Various systems and methods for detecting contrast agents where one path preferentially detects difference or motion signals and another path preferentially detects nonlinear energy are provided.

30 Claims, 1 Drawing Sheet

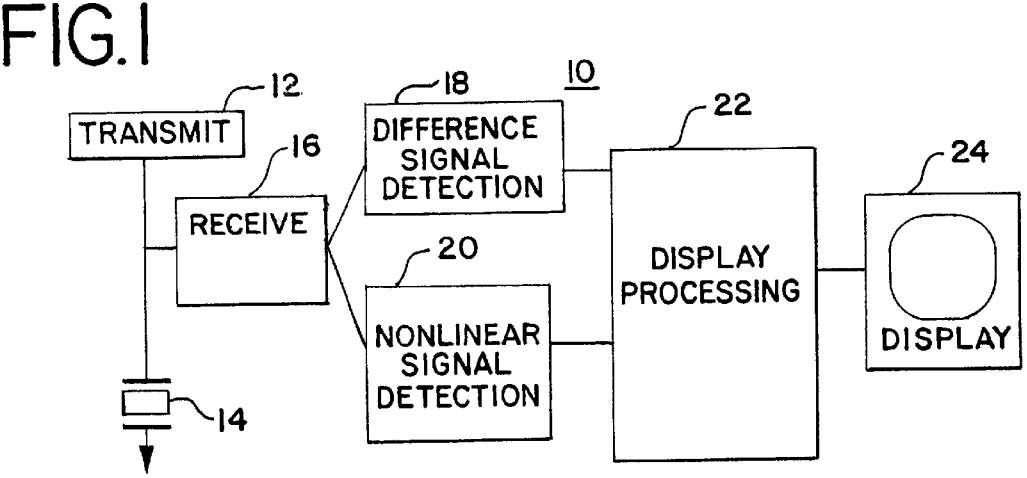
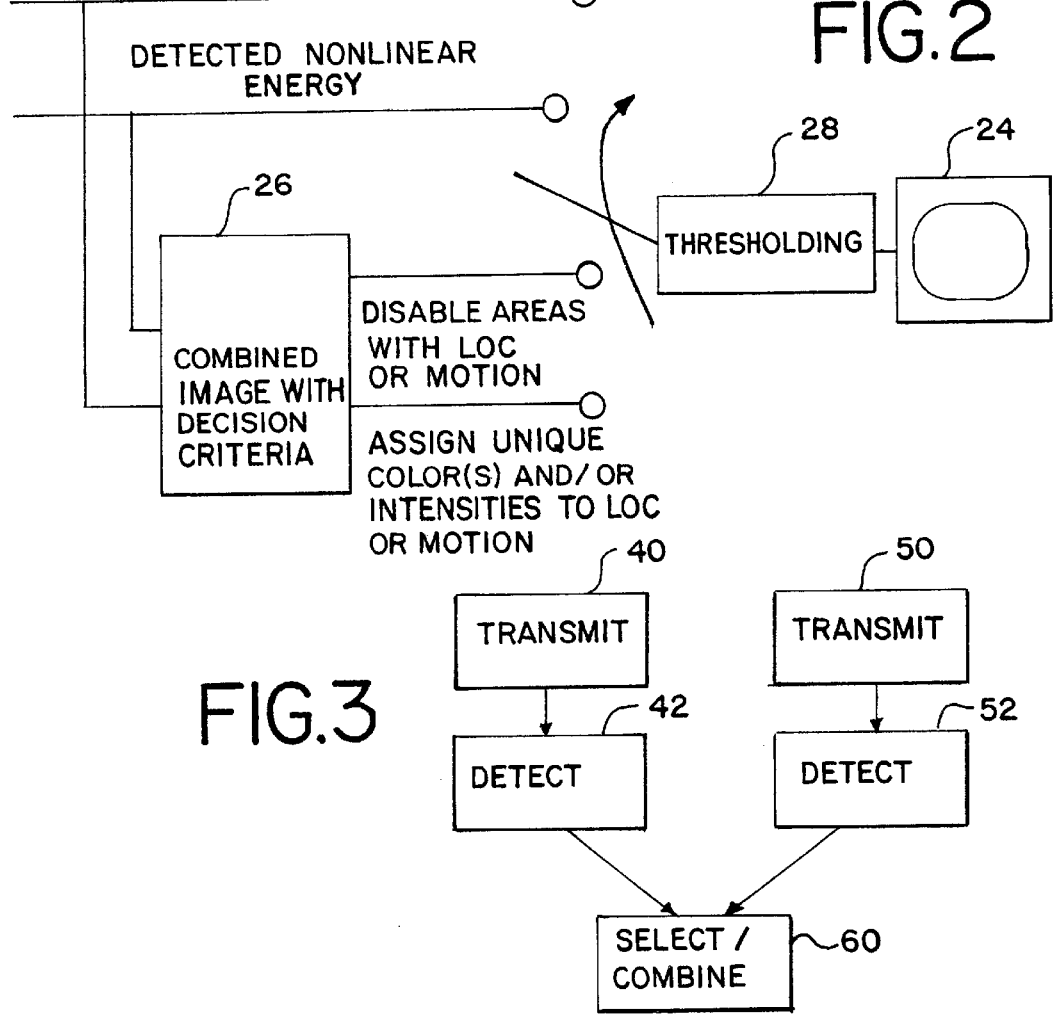

DUAL PROCESS ULTRASOUND CONTRAST AGENT IMAGING

BACKGROUND

The present invention relates to detecting ultrasonic contrast agents in medical diagnostic ultrasound imaging. Ultrasonic imaging of contrast agents with low transmit powers or low mechanical indices (MI) provides high frame rates by avoiding destruction of contrast agents. However, the returned signals are often weak. With higher acoustic pressures, agents are depleted in the imaging scan plane, and frame rates must be reduced to allow contrast agent to re-enter the scan plane. Higher returned signal levels associated with higher transmitted pressures produce improved image quality, however low frame rates hinder the clinicians ability to maintain a similar scan plane over time and monitor the blood flow in a suspicious area.

Myocardial perfusion, liver pathology, breast pathology, prostate pathology, and portions of the vascular system may benefit from improved contrast agent imaging, especially when high frame rates are achieved using low MIs. For example, the use of contrast agents can improve the assessment of cardiac wall motion and perfusion. Healthy blood flow in the myocardium can take up to 4–8 heartbeats to completely penetrate the entire heart muscle once injected contrast agent arrives in the major heart chambers. The blood filled with contrast agent enters the ventricle, or atria, and the detected agent in this blood is often displayed with extreme brightness due to the high concentration of agent and large blood volume. The blood that later circulates in the myocardium often shows up less bright due to the much smaller blood volume and smaller agent concentration. Small differences in myocardial perfusion, which may indicate areas of ischemia, are difficult to identify since the chambers are typically much brighter and the detected contrast agent in the chambers occupies a large area on the display. The human visual system is often overwhelmed and challenged to easily identify suspicious areas. Different display methods based on simple intensity thresholding may suppress the bright signals in the chambers. However, with this type of method, after the agent has already been detected, signals with similar magnitude may be suppressed in the myocardium as well as the chambers. Critical areas of interest in the myocardium can be suppressed in the display. A technique is needed that suppresses or eliminates the bright signals in larger chambers while maintaining signals in the myocardium.

As another example, differentiation between vessel sizes in abdominal liver imaging is clinically useful. Vascular anomalies, such as a potential hemangioma or heptacellular carcinoma, can be better understood by identifying the structure of vessels feeding a suspicious lesion. The use of contrast agents can improve the imaging of vascular anomalies. However, contrast agent imaging techniques may not specifically detect differences between large and small vessels. Two useful procedures that help a user discriminate between large and small vessels are: (1) to image the initial bolus of contrast agent immediately after an injection and (2) image intermittently while varying the transmit power levels. With the first procedure, the amount of time available is significantly limited. The initial bolus typically transverses the larger arterial vessels within 30–45 seconds. The collection of larger arterial vessels are observed before the contrast agent reaches the smaller micro-vasculature. After the initial bolus travels through the arterial vessels, the blood enters the smaller vessels and then begins to re-circulate. After 30–45 seconds, the image of a liver is often homogeneously bright, making identification of the vessels outside of the tiny microcirculation difficult. With the second procedure, varying the transmitted power changes the amount of bubble destruction in different sized vessels. However, the wash-in of fresh agent into the larger vessels is often short-lived. The period of contrast agent enhancement is diminished due to bubble depletion. When contrast agent is replenished in the microcirculation, the larger vessels again appear similar in intensity, or color, to the smaller vessels. If the transmitted power is raised enough to deplete the contrast agent in certain vessels of interest, the replenishment with new agent occurs quickly, making it difficult to observe the vascular structure. A technique is needed that uniquely identifies different sized vessels throughout the contrast agent examination.

BRIEF SUMMARY

The present invention is defined by the following claims, and nothing in this section should be taken as a limitation on those claims. By way of introduction, the preferred embodiments described below include a method and systems for detecting contrast agents. Differences between different sized vessels throughout the period of contrast agent enhancement are identified without significantly depleting the available agent. Further, the myocardium or microvasculature is uniquely identified from the larger chambers such as the ventricles or atria.

Dual detection paths or processes are used for imaging, such as one for detecting nonlinear contrast agent response and another for detecting differences between the responses to two or more substantially identically transmitted pulses. Where echoes from two or more pulses of acoustic energy are combined to detect the nonlinear response, the nonlinear response may also include signals originating from a loss-of-correlation (LOC) or motion between received pulses. These signals generated from LOC or motion can be produced from agent disruption where a second received echo is different from a first received echo due to a change in a bubble's shape (i.e., destruction), or from simple spatial translation between acoustic pulses as seen from the same spatial location, respectively. Together the detected differences signals and the nonlinear signals can differentiate contrast agent from tissue. Additional information is gained by detecting signals more responsive to differences due to LOC or motion without more significant nonlinear signal components. Each path detects different relative amounts of nonlinear response and responses caused by detected differences between echo signals of multiple pulses. Various systems and methods for detecting contrast agents where one path preferentially detects differences due to LOC or motion signals and another path preferentially detects nonlinear energy are provided.

Further aspects and advantages of the invention are discussed below in conjunction with the preferred embodiments.

BRIEF DESCRIPTION OF SEVERAL VIEWS OF THE DRAWINGS

The components and the figures are not necessarily to scale, emphasis instead being placed upon illustrating the principles of the invention. Moreover, in the figures, like reference numerals designate corresponding parts throughout the different views.

FIG. 1 is a block diagram of one embodiment of a system for detecting contrast agents with ultrasound energy.

FIG. 2 is a block diagram representing one embodiment of a system for outputting detected information.

FIG. 3 is a flow chart diagram representing one embodiment of a method for detecting contrast agents with ultrasound energy.

DETAILED DESCRIPTION OF THE PREFERRED EMBODIMENTS

The embodiments described below detect contrast agents using two or more detection methods where one method is more sensitive to differences due to LOC or motion at a spatial location than the other, and the other method is more sensitive to nonlinear responses. The outputs from at least two different detection methods are selected and/or combined for generating an image. Using the two methods allows for identification of contrast agent associated with small vasculature versus big vasculature or perfusion versus flow within chambers in tissue over a relatively long period of time using low power or low MI scanning.

FIG. 1 shows a system 10 for detecting contrast agents with ultrasound energy. The system 10 includes a transmit beamformer 12, a transducer 14, a receive beamformer 16, a difference signal detection path 18 (hereafter called the "difference path"), a nonlinear signal detection path 20 (hereafter called the "nonlinear path"), a display processor 22 and a display 24. Additional, different or fewer components may be provided. For example, a third detection path may be provided in parallel with the difference and nonlinear paths 18, 20. The difference and nonlinear paths 18, 20 operate in conjunction with the transmit and receive beamformers 12, 16 to detect data representing a substantially same spatial location at a substantially same time. A substantially same time refers to a time period which includes the time necessary to transmit a group of sequentially transmitted pulses. Transmissions used for the nonlinear path 20 are interleaved with or sequential to transmissions used for the difference path 18, and some transmissions can be shared, but the resulting data is obtained at a substantially same time.

The transmit beamformer 12 comprises a digital, analog, or digital and analog beamformer for transmitting pulses of acoustic energy along one or more scan lines. In one embodiment, the transmit beamformer comprises the transmit beamformer disclosed in U.S. Pat. No. 5,675,554, the disclosure of which is incorporated herein by reference. Amplifiers and delays control apodization and focus of waveforms generated by the transmit beamformer 12. The resulting transmit pulse is associated with an amplitude and a phase. For example, the transmit beamformer 12 is operable to generate a set or sequence of pulses along a same scan line. The sequence may include one, two, three or more pulses.

In one embodiment, the amplitude of all or a sub-set of the pulses is set to minimize destruction of contrast agents. By minimizing destruction of contrast agents for each sequence of pulses, imaging is provided without delay for further perfusion or reintroduction of contrast agents. Different sequences of pulses or pulses within a sequence may have a same power level or different power levels associated with maintaining contrast agents free of substantial destruction.

The sequences may include pulses with different amplitudes and/or different phases. Any difference in phase is in addition to phase adjustments for focusing or is a difference in phase of the transmit pulse at the focal point. In one embodiment, the sequence of pulses include inter-pulse amplitude modulation. The peak amplitude of one pulse in the sequence is different from another pulse in the sequence. The difference in amplitude is at the input to the transducer 14, the output of the transducer 14 or at the focal point within a region of interest. Alternatively, the pulses of a sequence have a substantially same amplitude and phase.

The receive beamformer 16 comprises digital, analog, or digital and analog components for receiving echo signals associated with scan lines in response to the transmitted pulses. In one embodiment, the receive beamformer 16 comprises the beamformer disclosed in U.S. Pat. No. 5,685,308, the disclosure of which is incorporated herein by reference. The receive beamformer 16 includes delays, amplifiers and a summer for applying apodization and focusing to generate echo signals representing spatial locations along each scan line. The amplifiers may be programmable filters to weight the echo signals of the receive beams, such as weighting echo signals responsive to different transmit beams differently for amplitude modulation. The phase of echo signals is maintained or changed. For changing the phase, the delays are adjusted to provide phasing in addition to focusing information. Alternatively, the phasing is changed after the summer, such as by a phase rotator, a sign change device or subtraction operations.

The nonlinear path 20 comprises one or more processors, digital signal processors, application specific integrated circuits, filters, adders, subtractors, inverters, detectors, digital components, analog components and combinations thereof. In one embodiment, the nonlinear path 20 includes a nonlinear detector operable to detect a nonlinear response characteristic of echo signals. As used herein, nonlinear includes any information that is received that does not behave linearly with transmit amplitude. For example, nonlinear includes harmonics (e.g. second or third harmonics), fractional harmonics (e.g. 3/2), sub-harmonics (e.g. 1/2), and nonlinear signals received within the fundamental frequency band (used for transmitting ultrasound pulses), and combinations thereof The nonlinear path 20 may comprise a B-mode, Doppler, flow or other processing path.

For detecting a nonlinear response characteristic in response to two or more transmit pulses, a filter is applied to each receive pulse and passes information at the desired harmonic or other frequency associated with the nonlinear response and reduces or removes information at other frequencies. Finite impulse response, infinite impulse response or other filters may be used. In alternative embodiments, the nonlinear response characteristic is obtained from combining echo signals responsive to different transmit pulses. For example, echo signals responsive to transmit pulses with opposite phases are added or echo signals responsive to transmit pulses with a same phase but different amplitude are subtracted. As another example, echo signals responsive to amplitude modulated and phase modulated transmit or receive pulses (i.e. transmit amplitudes that differ or receive weighting that differs) are combined.

The difference path 18 comprises one or more processors, digital signal processors, application specific integrated circuits, filters, adders, subtractors, inverters, detectors, digital components, analog components and combinations thereof. The difference path 18 may comprise a B-mode, Doppler, flow or other processing path. Although shown as two paths, a single processing unit can process both desired methods. In one embodiment, the difference path 18 includes a difference detector operable to detect a difference between echo signals representing a same spatial location and responsive to different transmit pulses along the same scan line. The difference path 18 of this embodiment detects a loss-of-correlation, or signal differences, between the echo signals, such as due to contrast agents changing shape or bursting, or due to tissue or contrast agent moving away from the same spatial location between the two transmit pulses. In one embodiment, the transmit pulse sequence for use by the difference path 18 utilizes substantially identical, multiple pulses such that any detectable differences are attributed to the insonified target (i.e., contrast agents and tissue) and not the system's 10 inability to generate substantially perfect unequal transmit pulses. The transmit pulses have a substantially same phase and amplitude. Within this context, the difference path includes the ability to detect a true loss-of-correlation or a difference at one spatial location due to movement (i.e. difference detected without any evidence of a correlation along a scan line). The function of the difference path is also to reject, or suppress, stationary targets such as contrast or tissue. Within this definition two received signals that are subtracted after transmitting two identical pulses function to detect differences due to target motion or LOC. Other sequences that use substantially identical transmitted pulses but receive weightings, or inter-pulse filtering, of unequal values also function to detect differences due to target motion or LOC. For example, many sequences used by the well known color flow imaging mode on commercial scanners meet the desired functionality of the difference path.

The outputs from the difference path 18 and the nonlinear path 20 are combined or selected for further processing or display by the processor 22. The processor 22 comprises a general processor, a digital signal processor, an application specific integrated circuit, a filter, other digital components, other analog components or a combination thereof. Many display formats may be used. Example formats include combining the two different outputs, separately displaying both outputs or selecting one output.

FIG. 2 shows one embodiment of the processor 22 with the display 24. The processor 22 includes a combiner 26 and a threshold device or selector 28. For each spatial location in a field of view, the selector 28 selects one of (a) a detected difference, loss-of-correlation or motion signal, (b) a detected nonlinear response signal, (c) a set value associated with disabling or displaying a zero value at the spatial location, and (d) a combination of the outputs of the two paths 18, 20. In alternative embodiments, fewer, different or additional selections are available.

In one embodiment, the selector 28 is operable to compare the output of the difference path 18 with a threshold. The nonlinear response characteristic is selected for display if the detected difference is below the threshold. The detected difference or loss-of-correlation output is selected if the detected difference is above the threshold. In another embodiment, a set value, such as a black or zero value is selected for spatial locations where the detected difference signals are above a threshold. The threshold value is application specific, selected by a user or determined by experimentation. Displayed information in other spatial locations comprise the detected nonlinear response or a combination of the nonlinear path and the difference path outputs. For some transmitted pressure levels, the detected nonlinear signals may contain loss-of-correlation information due to bubble disruption. For lower transmitted pressure levels, the detected nonlinear signals may not contain significant loss-of-correlation signals.

In another embodiment, the outputs from the two paths 18, 20 are combined. For example, a color code or different display intensities are assigned to detected difference or motion signals and gray scale information is assigned to the detected nonlinear responses. As yet another example, linear or nonlinear combinations of the outputs are provided by the combiner 26. Some such combinations are disclosed in U.S. Pat. No. 5,961,460, the disclosure of which is incorporated herein by reference. For use with the teachings of U.S. Pat. No. 5,961,460, the outputs from the two paths 18, 20 are the inputs to any of the various look-up tables. Look-up tables highlighting small or large vascular structures and reducing the brightness associated with large blood pools or vessels are used for assisting diagnosis.

FIG. 3 shows a flow chart of one embodiment of a method for detecting contrast agents with ultrasound energy. The method includes the acts of transmitting 40, 50 and detecting 42, 52 in two different paths, such as transmitting a sequence of pulses for nonlinear detection and transmitting a sequence of pulses for detecting differences, due to motion or loss-of-correlation. The detected data is combined or selected in act 60. The transmitting 40, 50 and detecting 42, 52 acts occur in a same imaging session as part of a same scan of a field of view and/or representing a same spatial location at a substantially same time. For example, the transmitting acts 40 and 50 are performed within 500 milliseconds (e.g. the first transmission for act 50 occurs within 500 milliseconds of the last transmission for act 40. The detecting acts 42 and 52 may also occur within 500 milliseconds. Additional, different or fewer acts may be provided.

In act 40, a first plurality of pulses are transmitted along a scan line. Three or more pulses may allow for more precise detection of nonlinear response with less noise or interfering signals from tissue. The pulses have a low power level, such as associated with minimizing destruction of contrast agents or maintaining contrast agents free of substantial destruction, but one, more or all of the pulses may have a higher power level. In one embodiment, the pulses within the plurality of pulses have different amplitudes and/or phases. For example, the amplitudes of the pulses are modulated to enhance second harmonic, nonlinear fundamental, or other nonlinear response. As another example, two pulses are transmitted with opposite phases. As yet another example, two pulses are amplitude modulated and associated with different phases, such as opposite or other phasing.

In act 42, a nonlinear response characteristic of echo signals responsive to the plurality of pulses is detected. In one embodiment, the information at a second or other harmonic of the fundamental transmit frequency is detected. Nonlinear signals at the fundamental may also be detected. Information at other frequency bands can be reduced by filtering each returned signal or combining echo signals and the resulting information is detected, such as with B-mode or other detection. Many other embodiments are possible, including embodiments using nonlinear response detection methods now known and later developed. Some examples are discussed below. The cited patents and applications are incorporated herein by reference. The examples include:

(a) Imaging with pulse inversion or phase inversion, such as disclosed in U.S. Pat. Nos. 5,951,478; 5,706,819; and 5,632,277. Echo signals associated with opposite polarities are added to reduce the fundamental frequency response and isolate even harmonic frequency response. For example, echo signals responsive to transmit pulses 180 degrees out of phase are added.

(b) "Pulse Inversion Doppler" or "Power Pulse Inversion" imaging, such as disclosed in U.S. Pat. No. 6,095,980. Broadband linear and nonlinear echo signal components are separated while simultaneously distinguishing the effects of motion. Ultrasonic echo signals are mapped in the radio frequency (i.e. time) domain to Doppler shift frequencies in the Doppler domain in a way that depends upon the linearity of the echoes by analyzing the phase shifts between successive echoes. The transmit sequence includes cyclically phase-varying waveforms. When the echoes of the ensemble are combined during Doppler processing, the resulting Doppler spectrum is divided into separate regions, with odd harmonics (e.g., linear signal components) residing in one region and even harmonics (e.g., second harmonic signal components) residing in another region.

(c) "Coherent Contrast" imaging, such as disclosed in U.S. Pat. No. 6,193,663. Receive beams are acquired from spatially distinct transmit beams. The receive beams alternate in type between at least first and second types across the region being imaged. The first and second types of receive beams differ in at least one scan parameter other than transmit and receive line geometry, and can for example differ in transmit phase, transmit or receive aperture, system frequency, transmit focus, complex phase angle, transmit code or transmit gain. Receive beams associated with spatially distinct ones of the transmit beams (including at least one beam of the first type and at least one beam of the second type) are then combined. In this way, many two or more transmit pulse techniques, including, for example, phase inversion techniques, synthetic aperture techniques, synthetic frequency techniques, and synthetic focus techniques, can be used while substantially reducing the frame rate penalty normally associated with such techniques. As used herein, "substantially along a scan line" includes transmission along adjacent scan lines used for detection along another scan line such as described for "coherent contrast imaging."

(d) Coded excitation imaging, such as disclosed in U.S. Pat. Nos. 6,241,674 and 6,213,947. A fundamental coded ultrasonic pulse is transmitted into a tissue. This pulse has a time-bandwidth product that is greater than 1 but less than 100. A receiver is coupled to the probe to receive an Nth harmonic echo signal from the tissue, and a compression filter compresses the harmonic echo signal with a compression function having a phase that varies about N times as fast as the fundamental coded ultrasonic pulse. In this way, the signal-to-noise ratio of the resulting image is increased. In another mode, first and second ultrasonic beams are transmitted into a body along first and second spatially distinct transmit beam directions and used with B-mode or motion detection processing. The two beams are coded with unique, preferably orthogonal, spatially invariant, nonlinear phase modulation codes and the second beam is transmitted before the first beam has left the tissue. Multiple spectral Doppler images from independent gates are generated. In yet another mode, first and second uniquely coded ultrasonic beams are launched into a body to focus at substantially the same point such that the two beams sample motion at different times. Unconventionally high velocity parameters are estimated and other motion parameters, including velocity parameters, may be estimated with improved accuracy. In yet another mode, first and second uniquely coded ultrasonic beams are transmitted into a body to focus preferentially at the same point where each beam originates from a subaperture and the receive signals are used with motion detection processing. In yet another mode, two or more coded ultrasonic beams are transmitted into the body with alternating polarities in a pulse inversion harmonic Doppler mode to improve the signal-to-noise ratio while imaging contrast agents (e) Higher order nonlinear imaging, such as various filtering, transmit, receive combination or other processes for detecting third or higher harmonic frequencies.

(f) "Power Modulation" imaging, such as disclosed in U.S. Pat. No. 5,577,505. The ultrasound response is measured in response to multiple excitation levels. The responses gathered from the multiple excitation levels are gain corrected in an amount corresponding to the difference in excitation levels, then subtracted. Because of this subtraction, most of the linear response is removed, and what remains corresponds to the non-linear response.

(g) "Contrast Pulse Sequences" imaging, such as disclosed in U.S. Pat. Nos. 6,494,841 (application Ser. No. 09/514,803 (filed Feb. 29, 2000) and Ser. No. 09/650,942 (filed Aug. 30, 2000)). A sequence of pulses are transmitted into a body, including at least two pulses that differ in amplitude and phase. Echo signals are received, beamformed, weighted and summed to suppress first order echoes. In one form, no two pulses of the sequence have the same amplitude and opposite phase. In another form, only linear echoes are suppressed. In a third form, second and third order echoes are preserved while linear echoes are suppressed. In another embodiment, three pulses, including at least two pulses of different amplitude and at least two pulses of differing phase, are transmitted. The larger-amplitude pulse is transmitted with a larger aperture and the smaller-amplitude pulses are transmitted with respective smaller subapertures. The subapertures are arranged such that the sum of the subapertures used for the smaller-amplitude pulses is equal to the aperture used for the larger-amplitude pulse. In this way, pulses of differing amplitudes are obtained without varying the power level of individual transducer elements, and precise control over pulse amplitude is provided.

(h) Improved contrast agent specificity with reverberation-suppression pulses, such as disclosed in U.S. Pat. No. 6,436,041 (application Ser. No. 09/746,690, filed Dec. 12, 2000). Fundamental or desired harmonic orders are suppressed by transmitting at least one reverberation-suppression pulse prior to the transmission of a multiple-pulse sequence. Receive signals associated with the pulses of the multiple-pulse sequence are acquired and combined using receive weights selected to suppress energy at either the fundamental or a desired harmonic of the fundamental.

In act 50, a plurality of pulses are transmitted substantially along the scan line used for the transmissions of act 40. The transmit pulses of act 50 include at least one pulse not included in the transmit pulses of act 40. In one embodiment, all of the plurality of pulses used in act 50 are different transmit pulses than the transmit pulses used in act 40. In alternative embodiments, one or more of transmit pulses of act 50 are also used as transmit pulses of the act 40, but at least one pulse is unique to the transmit pulses of act 50 or of act 40. In yet another alternative embodiment, the transmit pulses of act 40 are the same transmit pulses of act 50.

The transmit pulses of act 50 have substantially a same phase and amplitude. Substantially same is used herein to account for tolerances in performance of the system 10 and other noise or incidental variations. For example, three transmit pulses with a substantially same peak amplitude and phases are transmitted, as represent by the symbolism [1 1 1] where "1" indicates a general or relative amplitude. Having the same peak amplitude and phase better isolates differences. Any detected difference is a result of differences in the target, not the transmitted pulses. Transmit pulses with identical signal characteristics may provide better detection of target differences.

The transmit pulses have a low power level, such as associated with minimizing substantial destruction of contrast agents or maintaining contrast agents free of substantial destruction. The power level for the transmit pulses of act 50 is a same or different power level of any one of the transmit pulses of act 40.

In act 52, a difference between echo signals responsive to different transmit pulses of act 50 is detected. For example, a loss-of-correlation between transmit pulses is detected due to movement or destruction of contrast agents. This detected difference results in detecting moving or changing targets while rejecting stationary targets. In one embodiment, the echo signals responsive to the transmit pulses of act 50 are weighted prior to detection. The weights are chosen such that static targets and unwanted motion is rejected. For example, in response to three transmit pulses, the echo signals are weighted with 1, −2, 1 weights, respectively, as represented by [1 −2 1]. The values 1 and 2 correspond to relative amplitude weightings and the minus sign corresponds to subtraction or an opposite phase. The weighted echo signals are added, and the result is detected. In alternative embodiments, correlated motions, such as Doppler velocity, energy or variance, are detected.

Using the [1 1 1]*[1 −2 1] notation for the sequence described above, where the "*" symbol represents convolution, images may lack any displayed signals, i.e., may be black, unless motion or loss-of-correlation signals exist. With this notation, only the summed products from the convolution that include all the terms from the receive weightings (three in this case) are included. For this example, three pulses of equal amplitude and phase are transmitted. Three pulses are received, weighted, and added producing one output. Many other transmit and receive sequences may be used to detect the difference signals. For example, the receive weights may be convolved with the received echo signals to produce more than a single output, improving the signal-to-noise ratios or ability to suppress undesired slowly moving targets. An example is [1 1 1 1]*[1 −2 1]. Two outputs are produced. Further, many transmit sequences used for Doppler color flow imaging where multiple substantially identical pulses are transmitted for detecting velocities, variances, or other motion parameters can also be used to detect loss-of-correlation signals.

Many other combinations of transmit and detection sequences for both nonlinear detection and difference detection are possible. In one embodiment, nonlinear detection utilizing phase modulation across two or more transmitted pulses is provided. The nonlinear sequence is given by [1 −1 1 −1 1]*[r1 r2 r3 r4 r5] where the receive filter coefficient variables r1, r2, . . . r5 are of various possible values and where "−" in the transmit sequence represents a 180 degree or opposite phase. One example receive filter is [1 4 6 4 1]. The criteria for picking the filter coefficients is application dependent, but preferably provides sufficient signal sensitivity and suppression of undesired motion artifacts. The difference detection sequence is given by [1 −1 1 −1 1]*[1 0 −2 0 1]. The difference sequence may utilize the returned signals from three of the same five transmitted pulses utilized by the nonlinear transmit sequence. The three echo signals used are associated with transmit pulses having a substantially same phase and peak amplitude. With the above detection combination, two different processing methods are combined without any loss in frame rate since three of the same transmitted pulses are used by both methods.

Another combination is represented by [1 −1 1 1 1]*[1 2 1 0 0] for nonlinear detection and [1 −1 1 1 1]*[0 0 1 −2 1] for difference detection. These two sequences share the received signal from the third transmitted pulse, avoiding the need for a total of six transmitted pulses with receive filters for the two techniques of three coefficients each. Yet another combination is represented by [1−1]*[1 2 1] for nonlinear detection and [1 1 1]*[1 0 −1] for difference detection. These two sequences may be used where motion artifacts are tolerable or there is not significant motion present. Two further examples include [1 1 −1 1 1]*[1 0 2 0 1] for nonlinear detection and [1 1 −1 1 1]*[0 1 0 −1 0] for difference detection or [1 1 −1 1 1]*[0 1 2 1 0] for nonlinear detection and [1 1 −1 1 1]*[1 0 0 0 −1] for difference detection. For the [1 1 −1 1 1]*[0 1 2 1 0] for nonlinear detection and [1 1 −1 1]*[1 0 0 0 −1] for difference detection sequence, less loss-of-correlation information may be included in the nonlinear detection information and more loss-of-correlation may appear with the difference detection since less time exists between the pulses processed for the nonlinear detection and more time exists between the pulses processed for the difference detection. The nonlinear detection examples given above are sensitive to second harmonic signals, but other sequences for identifying other harmonics or the second harmonic may be used.

The examples above use uniform transmit pulse amplitude. Various embodiments using inter-pulse amplitude modulation of the transmit pulses for nonlinear detection are possible. In one embodiment, the sequences are represented as [0.5 −1 0.5 0.5 0.5]*[1 1 1 0 0] for nonlinear detection and [0.5 −1 0.5 0.5 0.5]*[0 0 1 −2 1] for difference detection. Other embodiments include: [0.5 −1 −1 −1 0.5]*[1 0 1 0 1] for nonlinear detection and [0.5 −1 −1 −1 0.5]*[0 1 −2 1 0] for difference detection; [0.5 1 0.5 0.5 0.5]*[1 −1 1 0 0] for nonlinear detection and [0.5 1 0.5 0.5 0.5]*[0 0 1 −2 1] for difference detection; [0.5 1 11 0.5]*[1 0 −1 0 1] for nonl detection and [0.5 1 1 1 0.5]*[0 1 −2 1 0] for difference detection; [0.5 −1 0.5 −1 0 −1]*[1 1 1 0 0 0] for nonlinear detection and [0.5 −1 0.5 −1 0 −1]*[0 1 0 −2 0 1] for difference detection. These embodiments are sensitive to nonlinear signals within the fundamental frequency band and higher order signals outside the fundamental frequency band, such as the second harmonic. They are also sensitive to loss-of-correlation signals since more than two received pulses are used. Examples of additional sequences that are included in this category are disclosed in the references discussed above at paragraphs (f), (g) and (h).

The transmit pulse sequences in the examples represented above use different numbers of common transmit pulses, such as the difference detection sequence having none, one, two or more or all of the same or common transmit pulses as the nonlinear detection sequence. Using non-shared or completely separate transmit pulses, improved detectability of loss-of-correlation signals or other nonlinear signals is obtained by using different signal characteristics, such as different pulse shapes, amplitudes, modulation frequencies, envelope modulation frequencies, envelope amplitudes, envelope amplitude profiles, envelope phase or envelope phase profiles. Completely separated transmit pulse sequences are represented by [A −A A]*[1 2 1] for nonlinear detection and [B B B]*[1 −2 1] for difference detection (i.e. a transmit pulse representation of [A −A A B B B]) or [A/2 −A A/2]*[1 1 1] for nonlinear detection and [B B B]*[1 −2 1] for difference detection, where A and B represent pulses having any of various characteristics listed above. Other three transmit pulse or more than three transmit pulse sequences may be used. Transmit sequences that use only one or two pulses are less desirable due to insufficient suppression of stationary or slowing moving targets.

The transmit pulses of either the sequence for nonlinear detection or the sequence for difference detection are transmitted at regular intervals. In other embodiments, the intervals are varied. The time between any two transmit pulses may vary over the total time to transmit all the required pulses of a sequence. For example, in the nonlinear detection sequence represented by [0.5 −1 0.5 0.5 0.5]*[1 1 1 0 0] and the nonlinear detection sequence represented by [0.5 −1 −1 −1 0.5]*[1 0 1 0 1], the time between the three transmit events used by the nonlinear detection differ by a factor of two (i.e. the time between the first and second pulses in the first sequence is half the time between the first and third pulses in the second sequence). Alternative strategies include varying the time between any unique set of two transmit events. In one embodiment, the time between transmit events three, four and five of the first sequence above is increased beyond the time between the transmit pulses one, two and three. Thus, with a difference sequence of [0.5 −1 0.5 0.5 0.5]*[0 0 1 −2 1] greater time is allowed to detect motion or LOC. This time variance may increase the amount of detectable difference signals due to motion, increasing the sensitivity. Maintaining the smaller time interval between transmit events one, two and three minimizes loss-of-correlation information that would also be detected by the nonlinear detection. This improves the preferential detection of nonlinear energy versus difference energy in each signal processing path.

In addition or as an alternative to increasing the time between transmit pulses described above, interleaving transmit pulses for one pulse sequence with transmit events for a different spatial location or scan line can increase intervals without lost frame rate. While waiting to transmit the next pulse in a sequence along one scan line, a transmit pulse associated with another sequence for a different scan line is transmitted. The system then returns to transmit a pulse on the original scan line. This process is analogous to the means used with color Doppler flow processing to detect low velocity flow without a significant loss in frame rates. Let $T_{ij}$ denote a transmit pulse for scan line i with j corresponding to the jth transmit pulse for the same line. The sequence of transmit pulses in chronological order for a line interleave factor of two for a sequence with five transmitted pulses, as an example, may be $T_{11}$ $T_{21}$ $T_{12}$ $T_{22}$ $T_{13}$ $T_{23}$ $T_{14}$ $T_{24}$ $T_{15}$ $T_{25}$. This sequence increases the time between any two jth events for scan line i by two, compared to the case without interleaving. Sequences with additional scan lines, fewer or additional transmit pulses for each scan line or combinations thereof may be used.

Another method to maintain high frame rates for sequences where the time between transmitted pulses is not constant is to alternately change the order of the transmitted pulses associated with different scan lines and interleave the transmitted pulses between the different scan lines. For the transmit pulse sequence [0.5 −1 0.5 0.5 0.5] discussed above, doubling the time between the three transmit pulses associated with the difference detection (e.g. the third, fourth and fifth pulses) for each line may introduce a loss in efficiency from 100% to 71% without interleaving. For two scan lines, $L_1$ and $L_2$, respectively, the following transmit ordering uses four blocks of time delay time i.e., "dead time", shown as four dots in this sequence. $L_1$ $L_1$ $L_1$ . $L_1$ . $L_2$ $L_2$ $L_2$ . $L_2$ . $L_2$. The efficiency drops to (1−4/14)×100, 77%. The efficiency is increased back to 100%, i.e., no dead time, by reversing the order of the transmitted pulses for the second scan line and interleaving the transmit pulses. $L_1$ $L_1$ $L_1$ $L_2$ $L_1$ $L_2$ $L_1$ $L_2$ $L_2$ $L_2$. This concept can be extended to other sequences and other desired time intervals between trans-mitted pulses to increase efficiency and therefore maintain high frame rates. The order of transmit pulses is varied as a function of scan line, effectively varying any of an order of multiple receive amplitudes, multiple receive phases, multiple transmit amplitudes, multiple transmit phases and combinations thereof as a function of scan line.

Transmit pulses in addition to the transmit pulses used for detection may be provided. In one embodiment, reverb-suppression transmit pulses are transmitted to minimize image artifacts. Acoustic energy associated with an earlier transmit pulse may interfere with the received signals primarily responsive to a subsequent transmit pulse. The additional energy from the earlier transmit pulse can introduce artifacts in an image. With the summation of paired transmit and receive products, some frequency components of the returned signals are expected to be zero or near zero. If additional energy corrupts some of the received echo signals, the final summation may not be zero or may be much larger than desired. For example, the sequence [0.5 −1 0.5]*[1 1 1] produces a zero value for linear fundamental energy when no reverberant energy is present. However, reverberant energy during the reception of the second and third echo signals, but not the first, produces a non-zero value since [0 0.5 −1]*[1 1 1] is not zero.

Two approaches may be used to minimize the impact of reverberant energy. In one approach, additional pulses are transmitted, but not used to receive echo signals, effectively priming the acoustic field to set up consistent reverberant energy between multiple received pulses. In another approach, particular pulse sequences may be used to satisfy the requirements for both the difference detection and the nonlinear detection while reducing the effects of reverberating acoustic energy. A few examples are included in the following table:

| desired sequence | improved sequence |
|---|---|
| Nonlinear detection [transmit] * [receive] | |
| Difference detection [transmit] * [receive] | |
| [0.5 −1 0.5 0.5 0.5] * [1 1 1  0 0] | [0.5 0.5 −1 0.5 0.5 0.5] * [o 1 1 1 0 0] |
| [same] * [0 0 1 −2 1] | |
| [0.5 0.5 0.5 −1 0.5] * [0  0 1 1 1] | |
| [same] * [1 −2 1 0 0] | [0.5 0.5 0.5 0.5 −1 0.5] * [o 1 −2 1 0 0] |
| [0.5 −1 0.5 0.5 0.5 0.5] * [1 1 1 0  0 0] | [0.5 0.5 −1 0.5 0.5 0.5 0.5] * [o 1 1 1 0 0 0]] |
| [same] * [0 0 0 1 −2 1] | [0.5 0.5 −1 0.5 0.5 0.5 0.5] * [o 0 0 0 1 −2 1] |
| [$0.5^1$ $0.5^2$ $0.5^1$ $0.5^2$ $0.5^1$ $0.5^2$ $-1^1$ $-1^2$ $0.5^1$ $0.5^2$] * [0 0 0 0 $1^1$ $1^2$ $1^1$ $1^2$ $1^1$ $1^2$] | — |
| [same] * [$1^1$ $1^2$ $-2^1$ $-2^2$ $1^1$ $1^2$ 0 0 0 0] | [$0.5^2$ $0.5^1$ $0.5^2$ $0.5^1$ $0.5^2$ $0.5^1$ $0.5^2$ $-1^1$ $-1^2$ $0.5^1$ $0.5^2$] * [o $1^1$ $1^2$ $-2^1$ $-2^2$ $1^1$ $1^2$ 0 0 0 0] |

In the table, the left column represents the desired sequence with the upper sequence in each cell representing the nonlinear detection and the lower sequence in each cell representing the difference detection. The right column shows replacement sequences where reverb-suppression pulses are used. The first 0.5 transmit pulse of each replacement sequence is an extra pulse transmitted but not associated with receiving an echo signal ("o" indicates lack of any reception). The italicized values indicate transmitted pulses used for receiving echoes but also used as a reverb-suppression pulse for another detection sequence. Some reverberation suppression sequences are not used for one of the two detection methods, as indicated by "–." In the second row, an additional transmit pulse of 0.5 is used to suppress artifacts associated with the nonlinear detection. In the third row, an extra transmit pulse is used to suppress artifacts associated with the difference detection. In the fourth row, an extra preceding pulse is used to suppress artifacts associated with the nonlinear detection and the last transmit pulse used for the nonlinear detection is also effective as a reverb-suppression pulse for the difference detection. In the last row, both an extra preceding pulse and a shared pulse are used to minimize reverberant artifacts. The superscripts indicate different line numbers corresponding to interleaved sequences.

Other embodiments are described in U.S. Pat. No. 6,436,041 (application Ser. No. 09/746,690, filed Dec. 12, 2000).

Other processes may be added to the above embodiments to further improve detectability of contrast agents. For example, signal parameter estimates, such as velocity estimates or variance estimates, identify unique characteristics of contrast agents. Velocity and variance estimates are obtained by using the transmit pulses used for difference detection. The same transmit pulses used for difference detection are also used for velocity detection, such as represented by [0.5 –1 0.5 0.5 0.5]*[1 1 1 0 0] for nonlinear detection, [0.5 –1 0.5 0.5 0.5]*[0 0 1 –2 1] for difference detection and [ 0.5 –1 0.5 0.5 0.5]*[0 0 1 1] for velocity or variance detection. In this example, a [1 1] filter is convolved ("*") with echo signals responsive to three transmit pulses, generating two outputs used to estimate the mean velocity and variance at each point in space along a scan line. In one embodiment, the velocity or variance estimates are used to further suppress areas in the display or used to color code unique areas in the display.

Another additional process is the transmission of ultrasound energy to destroy contrast agents. Destructive pulse sequences may be added to increase the sensitivity of the difference detection. For example, a large amplitude or high power destructive transmit pulse or pulses are transmitted between any two transmit events used to detect difference information. The destruction pulses may enhance the level of loss-of-correlation. Destruction pulses may also be transmitted before a set of transmit events.

Yet another additional process is estimating noise signals or tissue signals to further enhance the detectability of contrast agents. Estimates of noise characteristics may be obtained by receiving signals without transmitting acoustic energy. These estimates can be used as a reference for thresholding algorithms which help determine when an echo signal indicates desired information or should be included in a display. Any algorithm that is able to differentiate tissue from blood vessels, heart chambers, and similar structures may also be used to improve the detectability of contrast agents.

Another additional process is amplitude modulation between different transmit pulses using subapertures. Desired pressure levels that differ between transmit pulses may be derived by changing the number of elements active in a transducer in addition, or instead, of using different voltages. Improved nonlinear detectability may be provided by the use of subapertures. Two or more subapertures that add up to create a full aperture can be generated in several different ways. An example is the use of odd and even elements, such as represented by the transmit pulse sequence of [0.5e –1 0.5o 0.5o 0.5o], where "e" refers to the even element numbers, "o" refers to the odd element numbers, and the "–1" is obtained with a full aperture. The 0.5 amplitude values result from using half of the aperture, such as the even or odd elements.

Once the difference information and the nonlinear information are detected for each spatial location, the information is used for selection or comparison in act 60. For example, the difference is compared with a threshold. The difference data is selected for output and display if the difference is above the threshold. The nonlinear response information is selected if the detected difference is below the threshold. The threshold is user selected or automatically selected to better identify contrast agents in perfused tissue or small or large vasculature. As another example, the difference and nonlinear data is combined, such as averaging, weighted averaging or linear or nonlinear look-up table combination. As yet another example, the difference and nonlinear data is combined on the display, such as color coding in response to the difference information and intensity coding in response to the nonlinear data or vise versa. An image responsive to both the difference and the nonlinear response is generated.

In another embodiment, the difference is compared with a threshold. If the difference is above the threshold, a set value is output. For example, a null or value representing no signal is output. High difference values are used to mask the image or display a unique color, or lack of color, in an image. If the detected difference is below the threshold, then the nonlinear response is output. The nonlinear response likely indicates perfused tissue or small vasculature. The masking provided by the difference values avoids overwhelming the image with large vessels or blood pools containing contrast agents.

In addition to displaying an image generated from two or more different contrast detection methods, other images may be generated from all or a subset of the pulses in a sequence. For example, a fundamental or second harmonic B-mode image is generated from one of the pulses in a sequence. This B-mode image can be used as a displayed reference image and images from the contrast agent detection methods can be superimposed onto the B-mode image. More than one pulse from a sequence can also be used to form a B-mode image. Different receive weights associated with a separate receive filter may be used to generate the B-mode image with improved signal-to-noise ratio. For example, a receive filter of [1 –1 1 0 0] with the [0.5 –1 0.5 0.5 0.5] transmit pulse sequence generates a second harmonic B-mode image. Another receive filter of [0 0 1 1 1] may also be used with this same transmit sequence to generate a fundamental B-mode image. Other combinations of imaging using one or more of the transmit pulses may be provided.

In addition to the criteria used to display signals from the nonlinear and difference information, signals associated with other images may be used. B-mode image intensity may be used to further differentiate areas of interest. For example, the display of signals from the heart chambers can be suppressed by combining the information from the nonlinear technique, the difference technique, and a B-mode image. Strong nonlinear signals, strong difference signals, and weak B-mode signals may be used to identify the chambers. Myocardial signals may be preferentially displayed by identifying spatial locations associated with weak or no difference signals, strong nonlinear signals, and average B-mode intensities. As an alternative to binary display criteria, such as turning on and off a pixel, these same signals modulate displayed values. For example, the brightness of the display responsive to the difference and nonlinear detection paths is increased for spatial locations with a strong B-mode intensity. The brightness is decreased in response to a weak B-mode intensity. Other combinations and selections of any of the detected data may be used.

While the invention has been described above by reference to various embodiments, it should be understood that many changes and modifications can be made without departing from the scope of the invention. It is therefore intended that the foregoing detailed description be understood as an illustration of the presently preferred embodiment of the invention, and not as a definition of the invention. It is only the following claims, including all equivalents, that are intended to define the scope of this invention.

What is claimed is:

1. A method for detecting contrast agents with ultrasound energy, the method comprising the acts of:
   (a) detecting motion or loss-of-correlation between first and second pulses in response to multiple pulses having substantially a same phase and amplitude; and
   (b) detecting nonlinear response in response to third and fourth inter-pulse amplitude modulated pulses;
   wherein (a) and (b) are performed within 500 milliseconds.

2. The method of claim 1 wherein (a) comprises detecting moving targets while rejecting stationary targets in response to the multiple pulses.

3. The method of claim 1 wherein (b) comprises detecting in response to the third and fourth amplitude modulated pulses, the third and fourth amplitude modulated pulses having different phases.

4. The method of claim 1 further comprising:
   (c) transmitting the first and second pulses of (a) at a first low power level; and
   (d) transmitting the third and fourth amplitude modulated pulses of (b) at a second low power level;
   wherein the first and second power levels comprise one of same and different power levels, the same and different power levels associated with maintaining contrast agents free of substantial destruction.

5. The method of claim 1 further comprising:
   (c) transmitting the first and second pulses and a fifth pulse of (a) with peak amplitudes [1 1 1]; and
   (d) weighting first, second and third receive echo signals responsive to the first, second and fifth pulses of (a) with first, second and third weights, respectively, corresponding to relative amplitudes and phases of [1 −2 1].

6. The method of claim 1 further comprising:
   (c) transmitting reverberation suppression pulses.

7. The method of claim 1 further comprising:
   (c) varying an order of one of multiple receive amplitudes, multiple receive phases, multiple transmit amplitudes, multiple transmit phases and combinations thereof as a function of scan line.

8. The method of claim 1 further comprising:
   (c) transmitting the first and second pulses of (a); and
   (d) transmitting the third and fourth amplitude modulated pulses of (b) wherein the second and third pulses comprise the same pulse and the first and fourth pulses comprise different pulses.

9. The method of claim 1 further comprising:
   (c) comparing detected motion or loss-of-correlation responsive to (a) with a threshold;
   (d) selecting the detected motion or loss-of-correlation if the detected motion or loss-of-correlation is above the threshold; and
   (e) selecting detected nonlinear response of (b) if the detected motion or loss-of-correlation is below the threshold.

10. The method of claim 1 further comprising:
    (c) selecting one of the difference and the nonlinear response for display at a spatial location.

11. The method of claim 1 further comprising:
    (c) combining the motion or loss-of-correlation and the non-linear response.

12. The method of claim 1 further comprising:
    (c) generating an image responsive to both the motion or loss-of-correlation and the nonlinear response.

13. The method of claim 12 wherein (c) comprises generating an image responsive to the difference, the non-linear response and a B-mode intensity.

14. The method of claim 1 further comprising:
    (c) comparing the motion or loss-of-correlation with a threshold;
    (d) outputting a set value if the motion or loss-of-correlation is above the threshold; and
    (e) selecting the nonlinear response if the detected motion or loss-of-correlation is below the threshold.

15. A system for detecting contrast agents with ultrasound energy, the system comprising:
    a first detector for detecting motion or loss-of-correlation between first and second pulses in response to multiple pulses having substantially a same phase and amplitude; and
    a second detector for detecting nonlinear response in response to third and fourth amplitude modulated pulses;
    wherein the first and second detectors are operable to detect within 500 milliseconds.

16. The system of claim 15 further comprising:
    a transmit beamformer operable to transmit at a first low power level the first and second pulses and to transmit the third and fourth amplitude modulated pulses at a second low power level;
    wherein the first and second power levels comprise one of a same power level and different power levels, the same and different power levels associated with maintaining contrast agents free of substantial destruction.

17. The system of claim 15 further comprising:
    a processor operable to compare detected motion or loss-of-correlation output from the first detector with a threshold and select the detected motion or loss-of-correlation if the detected motion or loss-of-correlation is above the threshold, but select detected nonlinear response output from the second detector if the detected motion or loss-of-correlation is below the threshold.

18. A method for detecting contrast agents with ultrasound energy, the method comprising the acts of:
    (a) detecting motion or a loss-of-correlation between first and second pulses in response to multiple pulses having substantially a same phase and amplitude; and
    (b) detecting nonlinear energy in response at least three pulses, a first one of the at least three pulses having a different phase than a second one of the at least three pulses;

wherein (a) and (b) are performed within 500 milliseconds.

19. The method of claim 18 wherein (b) comprises detecting nonlinear response in response to amplitude modulated pulses.

20. The method of claim 18 further comprising:
   (c) transmitting the first and second pulses and a fifth pulse of (a) with peak amplitudes [1 1 1]; and
   (d) weighting first, second and third receive echo signals responsive to the first, second and fifth pulses of (a) with first, second and third weights, respectively, corresponding to relative amplitudes and phases of [1 −2 1].

21. The method of claim 18 further comprising:
   (c) comparing detected motion or loss-of-correlation responsive to (a) with a threshold;
   (d) selecting the detected motion or loss-of-correlation if the detected motion or loss-of-correlation is above the threshold; and
   (e) selecting detected nonlinear response of (b) if the detected motion or loss-of-correlation is below the threshold.

22. The method of claim 18 wherein (a) comprises detecting moving targets while rejecting stationary targets.

23. The method of claim 18 wherein (a) comprises detecting a loss-of-correlation.

24. The method of claim 18 wherein (a) comprises transmitting the first and second pulses at a first low power level, and (b) comprises transmitting the at least three pulses at a second low power level;
   wherein the first and second power levels comprise one of a same power level and different power levels, the same and different power levels both associated with maintaining contrast agents free of substantial destruction.

25. The method of claim 18 further comprising:
   (c) transmitting reverberation suppression pulses.

26. The method of claim 18 further comprising:
   (c) varying an order of one of multiple receive amplitudes, multiple receive phases, multiple transmit amplitudes, multiple transmit phases and combinations thereof as a function of scan line.

27. The method of claim 18 wherein the second pulse of (a) comprises one of the at least three pulses of (b) and the first pulse of (a) is not included as any of the at least three pulses of (b).

28. A system for detecting contrast agents with ultrasound energy, the system comprising:
   a first detector for detecting motion or a loss-of-correlation between first and second pulses in response to multiple pulses having substantially a same phase and amplitude; and
   a second detector for detecting nonlinear energy in response at least three pulses, a first one of the at least three pulses having a different phase than a second one of the at least three pulses;
   wherein the first and second detectors are operable to detect within 500 milliseconds.

29. The system of claim 28 further comprising:
   a processor operable to compare detected motion or loss-of-correlation output from the first detector with a threshold and select the detected motion or loss-of-correlation if the detected motion or loss-of-correlation is above the threshold, but select detected nonlinear response output from the second detector if the detected motion or loss-of-correlation is below the threshold.

30. The system of claim 28 further comprising:
   a transmit beamformer operable to transmit the first and second pulses and a fifth pulse with at a first peak amplitude represented as [1 1 1]; and
   wherein the first detector is operable to weight first, second and third receive echo signals responsive to the first, second and fifth pulses with first, second and third weights, respectively, corresponding to relative amplitudes and phases of [1 −2 1].

* * * * *